United States Patent
Lauf et al.

(10) Patent No.: US 11,234,739 B2
(45) Date of Patent: Feb. 1, 2022

(54) FACET WEDGE, WEDGE BLOCKING PLATE AND METHOD OF INSTALLATION

(71) Applicant: Life Spine, Inc., Huntley, IL (US)

(72) Inventors: Garrett D. Lauf, Hampshire, IL (US); Daniel P. Predick, West Lafayette, IN (US); Michael S. Butler, St. Charles, IL (US); Zeshan Hyder, Munster, IN (US)

(73) Assignee: LIFE SPINE, INC., Huntley, IL (US)

( * ) Notice: Subject to any disclaimer, the term of this patent is extended or adjusted under 35 U.S.C. 154(b) by 217 days.

(21) Appl. No.: 16/663,320

(22) Filed: Oct. 24, 2019

(65) Prior Publication Data

US 2020/0170686 A1 Jun. 4, 2020

Related U.S. Application Data

(60) Provisional application No. 62/749,894, filed on Oct. 24, 2018.

(51) Int. Cl.
*A61B 17/70* (2006.01)
*A61B 17/86* (2006.01)

(52) U.S. Cl.
CPC ........ *A61B 17/7064* (2013.01); *A61B 17/864* (2013.01); *A61B 17/8605* (2013.01)

(58) Field of Classification Search
CPC ............ A61B 17/7064; A61B 17/8605; A61B 17/864; A61B 17/8042; A61B 17/808; A61B 17/92; A61B 17/7059; A61B 17/809; A61F 2/447; A61F 2/4455; A61F 2/4611; A61F 2/3094; A61F 2002/30433; A61F 2002/30772; A61F 2002/30578; A61F 2002/30785; A61F 2002/30507; A61F 2002/30787; A61F 2002/30607; A61F 2002/4615; A61F 2002/30904;
(Continued)

(56) References Cited

U.S. PATENT DOCUMENTS

| | | | |
|---|---|---|---|
| 2013/0060337 A1* | 3/2013 | Petersheim | ........ A61B 17/8042 623/17.16 |
| 2013/0131726 A1 | 5/2013 | Suh et al. | |

(Continued)

FOREIGN PATENT DOCUMENTS

EP 3058898 A1 8/2016

*Primary Examiner* — Pedro Philogene
(74) *Attorney, Agent, or Firm* — Foley & Lardner LLP

(57) ABSTRACT

An implant and method for spinal facet joint stabilization uses a wedge and plate adapted to accept prongs of a surgical instrument for installing the implant into a posterior spinal facet joint. The wedge has an anterior end with a threaded bore. A notch in each lateral side of the plate aligns with a groove in each lateral side of the wedge. Each notch and groove pair receives a prong of the surgical instrument to hold the wedge and plate during implantation. A superior tube of the surgical instrument supports a superior rod having an end configured for installing a bone screw attaching the plate to the superior vertebra of the spinal facet joint. An inferior tube of the surgical instrument supports an inferior rod having an end configured to attach to the threaded bore of the wedge along with the plate during introduction of the implant into the spinal facet joint, and installing the set screw to attach the plate to the wedge.

16 Claims, 10 Drawing Sheets

(58) Field of Classification Search
CPC .... A61F 2002/30482; A61F 2002/4622; A61F 2002/30576; A61F 2002/30843; A61F 2002/308; A61F 2002/30593
See application file for complete search history.

(56) References Cited

U.S. PATENT DOCUMENTS

| | | | | |
|---|---|---|---|---|
| 2014/0107785 A1* | 4/2014 | Geisler | ............. | A61F 2/442 623/17.16 |
| 2015/0230834 A1* | 8/2015 | Cannestra | ......... | A61B 17/7064 606/247 |
| 2016/0235546 A1* | 8/2016 | Cheng | ............. | A61F 2/4465 |

* cited by examiner

FACET WEDGE, WEDGE BLOCKING PLATE AND METHOD OF INSTALLATION

CROSS-REFERENCE TO RELATED APPLICATIONS

This U.S. non-provisional patent application claims the benefit of and/or priority under 35 U.S.C. § 119(e) to U.S. provisional patent application Ser. No. 62/749,894 filed Oct. 24, 2018 titled "Facet Wedge, Wedge Blocking Plate and Method of Installation," the entire contents of which is specifically incorporated herein by reference.

FIELD OF THE INVENTION

The present invention relates to orthopedic devices for the spine such as spine implants and their method of installation and, more particularly, to spine implants and their method of installation directed to facet joints of the spine.

BACKGROUND OF THE INVENTION

Vertebrae of the spine are linked to one another through an intervertebral disc, a left facet joint, and a right facet joint. This joint combination controls movement of the vertebrae relative to one another. Each adjacent vertebrae pair has a left facet joint and a right facet joint. The left facet joint has a pair of articulating surfaces located on the left side of the vertebrae, while the right facet joint has a second pair of articulating surfaces located on the right side of the vertebrae. Each pair of articulating surfaces includes a superior articular surface and an inferior articular surface. Together, the superior and inferior articular surfaces of adjacent vertebra form the facet joint. Being synovial joints, each facet joint is surrounded by a capsule of connective tissue and produces a fluid to lubricate the joint. The joint surfaces are coated with cartilage allowing the joints to articulate relative to one another.

Facet joints of the spine are in almost constant motion. Because of this, spinal facet joints in many people simply wear out. When facet joints become worn or torn, the cartilage may become thin or disappear. This can cause a reaction of the bone of the joint underneath—producing, e.g., overgrowth of bone spurs, an enlargement of the joints, and causing back pain. In other instances, the facet joint undergoes degradation and/or deterioration due to disease, injury, use, or other cause. All of the above and other conditions are commonly referred to as "spinal facet joint disease," "spinal facet joint syndrome," "spinal facet joint condition" or other names, and are hereinafter collectively, "spinal facet joint disorders" or simply "facet joint disorders." Spinal facet joint disorders are thus some of the most common of all recurring neck and back problems, with some of them causing serious physical symptoms such as severe pain, reduced immobility, and even disability.

One form of treatment for spinal facet disorders is surgery. A commonly used surgical method involves stabilizing/immobilizing the spinal facet joint through fusion of the spinal facet joint. Spinal facet joint fusion uses an implant that is installed on or relative to the spinal facet joint. Allograft or other appropriate material for promoting bone fusion may or may not be introduced into or carried by the implant. A configured body is delivered to the facet joint with a plate that is fastened to the configured body and to one or more of the affected adjacent vertebrae at or in the facet joint for stabilizing and restricting movement of the facet joint.

Current implants for spinal facet joint stabilization provide reasonable mechanical stability, but there is room for improvement. Accordingly, there is a need for a spine implant and installation instrumentation that can facilitate safe and effective stabilization and/or immobilization of a spinal facet joint.

SUMMARY OF THE INVENTION

The present invention is an implant for stabilizing and/or immobilizing a facet joint of the spine, a surgical instrument for installing the implant, a surgical kit for stabilizing and/or immobilizing a spinal facet joint, and a method of stabilizing and/or immobilizing a facet joint of a spine using the present implant and surgical instrument.

The implant includes a wedge, a plate, and a set screw (the implant components), the wedge and plate having cooperating structure for receiving arms, prongs, tangs, projections or the like of the surgical installation instrument that holds the implant during installation.

The set screw is characterized by an externally threaded cylindrical body defining a first set screw end and a second set screw end opposite the first set screw end, with a socket in the second set screw end.

The wedge is characterized by a posterior end, an anterior end, a superior side, an inferior side, a first lateral side, and a second lateral side. The first lateral side has a first groove that extends a first distance along the first lateral side from the anterior end of the wedge towards the posterior end. The second lateral side has a second groove that extends a second distance along the second lateral side from the anterior end of the wedge towards the posterior end. A threaded bore is disposed in the anterior end that is adapted to receive the externally threaded cylindrical body of the set screw.

The plate is characterized by a front side, a rear side, a superior end, an inferior end, a third lateral side, a fourth lateral side, a superior bore in the superior end extending from the front side to the rear side and adapted to receive a bone screw, and an inferior bore in the inferior end extending from the front side to the rear side and adapted to receive the set screw.

The third lateral side of the plate has a first notch that extends from the front side to the rear side. The fourth lateral side of the plate has a second notch that extends from the front side to the rear side.

The first notch in the third lateral side of the plate aligns with the first groove of the first lateral side of the wedge to receive a first prong of the implant installation tool/surgical instrument. The second notch in the fourth lateral side of the plate aligns with the second groove of the second lateral side of the wedge to receive a second prong of the implant installation tool/surgical instrument.

The kit for spinal facet stabilization surgery comprises the present spine implant (including the bone screw) and the surgical installation instrument and components.

The method of spinal facet joint surgery for joint stabilization, includes providing the present spine implant, providing the present surgical installation instrument, and using the surgical installation instrument to install the spine implant on a target spine facet joint.

Further aspects of the present invention will become apparent from consideration of the drawings and the following description of forms of the invention. A person skilled in the art will realize that other forms of the invention are possible and that the details of the invention can be modified in a number of respects without departing from the inventive concept. The following drawings and description are to be regarded as illustrative in nature and not restrictive.

BRIEF DESCRIPTION OF THE DRAWINGS

The features, characteristics, structures, elements and/or the like of the present invention will be more fully understood from the following detailed description taken in conjunction with the accompanying drawings, wherein.

DETAILED DESCRIPTION OF THE INVENTION

An exemplary embodiment will now be described to provide an overall understanding of the principles of the structure, function, manufacture, and use of the devices and methods disclosed herein. Those skilled in the art will understand that the devices and methods specifically described herein and illustrated in the accompanying drawings are non-limiting exemplary embodiments and that the scope of the present invention is defined solely by the claims. The features illustrated and/or described in connection with an embodiment may be combined with the features of other embodiments. Such modifications and variations are intended to be included within the scope of the present invention, but not limiting thereof.

In general, the spinal implant disclosed herein is configured for placement within or in between a facet joint, particularly, but not necessarily, in a posterior manner for spine stabilization and/or fusion. The spinal implant is configured to be placed in the plane of the facet joint, between the superior articular process and the inferior articular process of the facet joint. A mechanical spacer or wedge of the implant is provided in the facet joint between the inferior and superior articular processes, while a plate attached to the mechanical spacer is attached to the superior articular process. As such, the implants function to reduce or prevent sliding motion between the joint surfaces of the superior and inferior surface of the facet joint. The present spine implant also stabilizes the facet joint by distracting the facet faces and placing the joint capsule in tension. Components of the spine implant can be adapted in various manners (e.g., selection of material, dimensions, surface features, etc.) so as to provide a spine implant capable of adapting to various facet joint configurations. Additionally, various components of the spine implant can include a fusion-promoting bioactive material, allograft, or the like capable of actively promoting bone growth.

FIGS. 1-7 show various views of a spine implant (implant), generally designated 10, configured and/or adapted for use in stabilizing, immobilizing, fusing, or otherwise surgically treating (collectively, "stabilizing") a facet joint of the spine. The implant 10 is made from a biocompatible material. One or more of the various constituents, components, elements, or the like (collectively, "components") of the implant 10 and the surgical instrument 60 (see, e.g., FIGS. 8-10) may be formed, printed, stamped, molded, and/or otherwise fabricated using biocompatible materials appropriate for spine implants. Without limitation, the implant 10 may be made of stainless steel, titanium, and/or an alloy of same.

Figure 1:
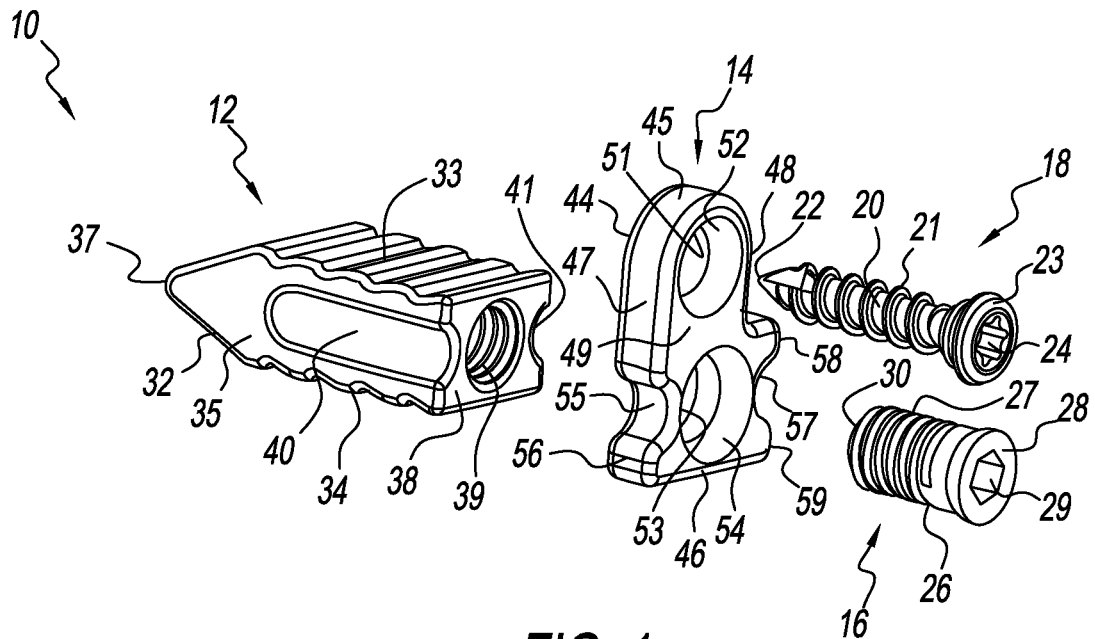
FIG. 1 is an exploded view of an implant for stabilizing and/or immobilizing a facet joint of the spine according to the principles of the present invention.
Figure 2:
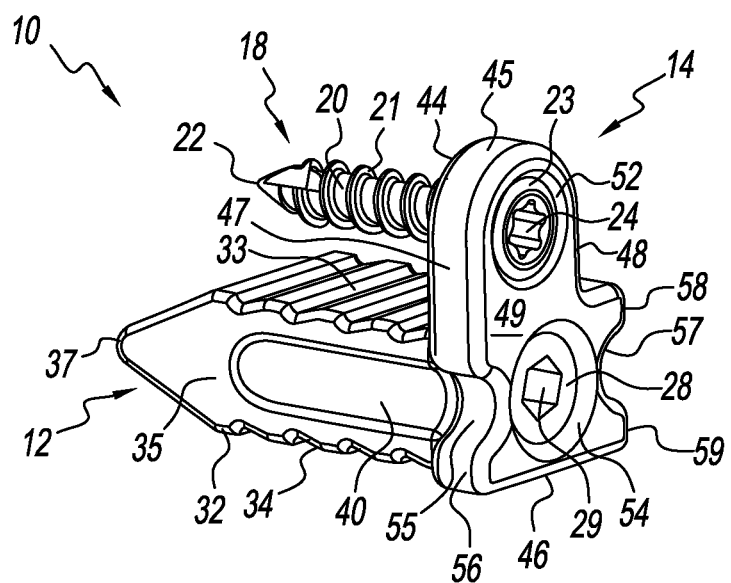
FIG. 2 is a view of the implant of FIG. 1, assembled.
Figure 3:
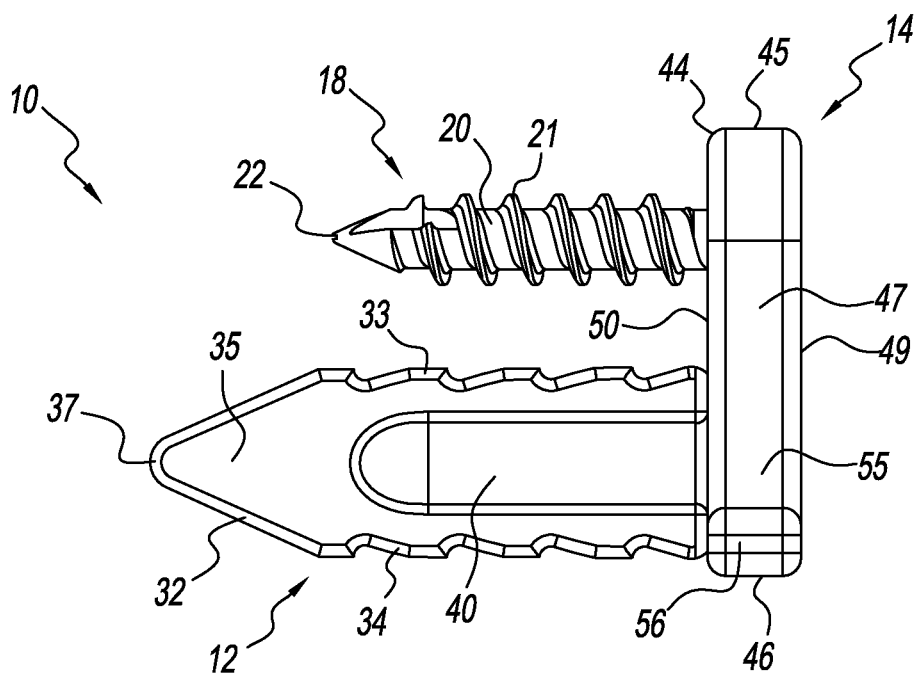
FIG. 3 is a side view of the implant of FIG. 2.
Figure 4:
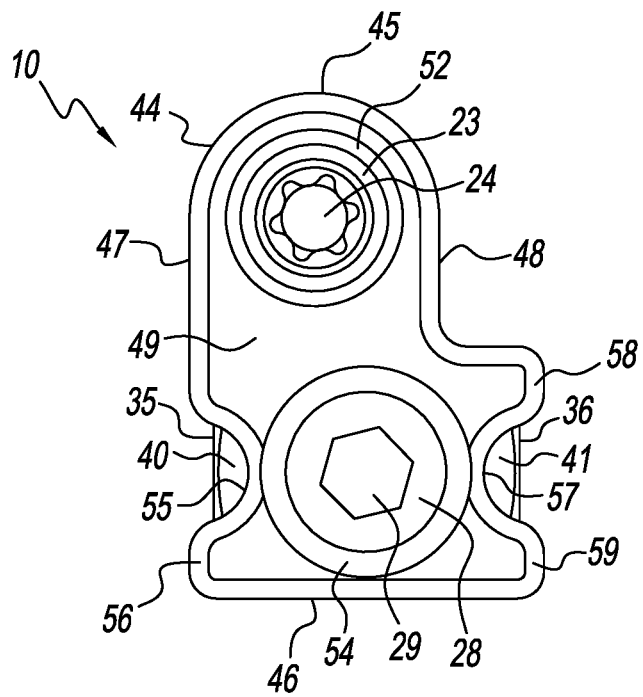
FIG. 4 is a front view of the implant of FIG. 2.

FIG. 1 provides an exploded view of the components of the implant 10. The implant 10 includes a mechanical spacer or wedge 12, a plate 14, and a set screw 16. The wedge 12 is received in the facet joint space DS (see, e.g. FIGS. 15-20), between the superior articular process of the superior vertebra V1 and the inferior articular process of the inferior vertebra V2. A bone screw 18 is used to attach the plate 14 to a superior articular process of a facet joint (see, e.g., FIGS. 13-15) and may or may not be considered part of the implant 10, but forms a part of a kit for spinal facet joint stabilization along with the wedge 12, plate 14, and set screw 16, and as otherwise noted. The bone screw 18 is particularly used to attach the plate 14 to the superior articular process of a superior vertebra V1. The set screw 16 is used to attach the plate 14 to the wedge 10. FIGS. 2-4 show the implant 10 assembled with the bone screw 18 received in the plate 14.

The wedge 12 is characterized by a generally cuboid body 32 having a superior side 33, an inferior side 34 opposite to the superior side 33, a generally planar anterior end 38, a protruding posterior end 37, a first lateral side 35, and a second lateral side (not discerned in the figures). The superior side 33 and the inferior side 34 are preferably, but not necessarily, textured. The texturing facilitates positive reception of the wedge 12 into the facet joint area DS. In one form, and as shown in the figures, the superior side 33 and the inferior side 34 have serrations. The serrations are angled to provide anti-back out properties.

A first groove, channel, elongated concavity, or the like 40 (collectively, "groove") is disposed in the first lateral side 35 of the wedge body 32 from the anterior end 38 towards the posterior end 37. The first groove 40 extends co-axial with a longitudinal axis of the cuboid implant body 32. A second groove, channel, elongated concavity, or the like 41 (collectively, "groove") is disposed in the second lateral side of the wedge body 32 from the anterior end 38 towards the posterior end 37. The second groove 41 extends co-axial with a longitudinal axis of the cuboid implant body 32. An internally threaded bore 39 is also provided in the anterior end 38. The internally threaded bore 39 is configured/adapted to receive the set screw 16, a threaded end 73 of a surgical component of the present surgical instrument/tool 60 such as an instrument rod 72 (see, e.g., FIG. 15) or other threaded component. The first and second grooves 40, 41 help the surgical instrument 60 hold the wedge 12 during installation.

The set screw 16 is characterized by an externally threaded cylindrical body 27 having a distal end 30 and a proximal end 28, the proximal end 28 defining a head. The head 28 has a socket 29 configured for engagement with one or more components (e.g., rod 76—see, e.g., FIG. 16) of the surgical instrument 60. The externally threaded cylindrical body 27 has a first diameter. The head 28 has a second diameter that is greater than the first diameter. The set screw 16 has a neck 26 that angles between the first diameter of the head 28 and the second diameter of the externally threaded cylindrical body 27.

The bone screw 18 is characterized by an elongated shank 20 having a tip 22 on a distal end of the shank 20, and a head 23 on a proximal end of the shank 20. External threading 21 is provided on the shank 20 between the tip 22 and the head 23. The threading 21 is configured for reception in vertebral bone. The head 23 has a socket 24 configured for engagement with one or more components (e.g., rod 74—see, e.g., FIG. 14) of the surgical instrument 60, particularly, but not necessarily, for installing the bone screw 18.

Figure 5:
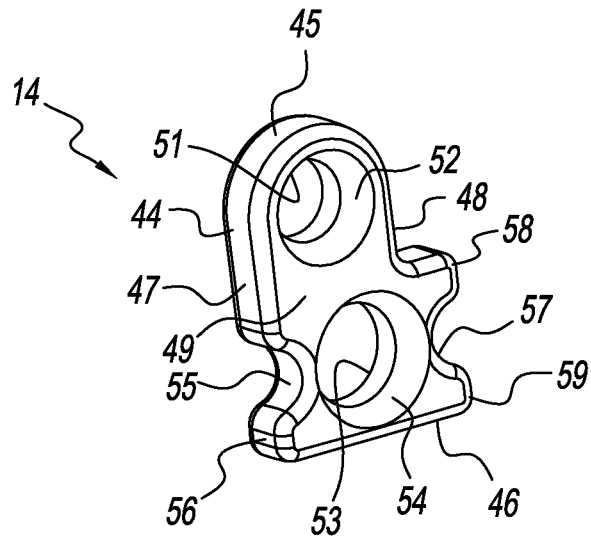
FIG. 5 is a view of the plate of the implant of FIG. 1.
Figure 6:
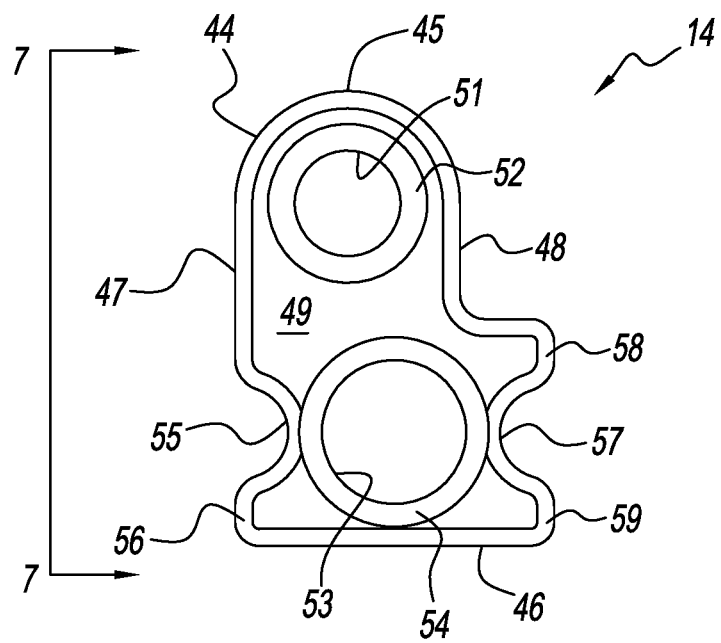
FIG. 6 is a front view of the plate of FIG. 5.
Figure 7:
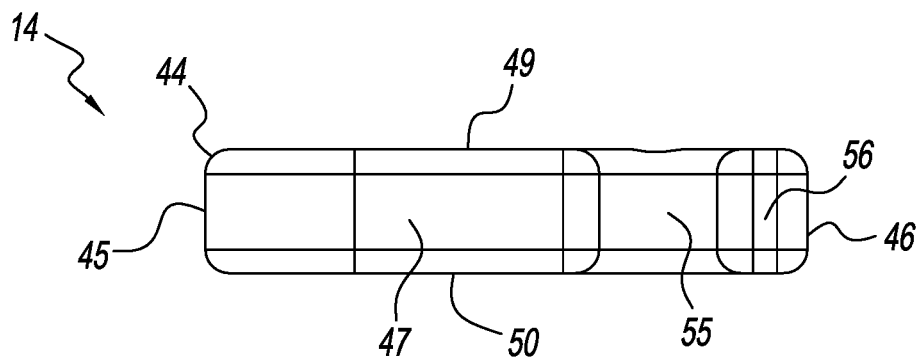
FIG. 7 is a side view of the plate of FIG. 5.

As additionally seen in FIGS. 5-7, the plate 14 is characterized by a body 44 having a generally rounded superior end 45 and a generally flat or planar inferior end 46. The body 44 further defines a first lateral side 47, a second lateral side 48, a front or anterior side 49 and a rear or posterior side 50. The body 44 is not relatively thick (see, e.g. FIG. 7). A bore 51 is provided at the superior end 45 of the body 44, while a bore 53 is provided at the inferior end 46 of the body 44. A countersink 52 is provided around the bore 51 at the anterior side 49, while a countersink 54 is likewise provided around the bore 53 at the anterior side 49. The countersinks 52, 54 define pockets for heads of components (e.g., bone screw heads and set screw heads). The superior bore 51 is sized and configured to allow the shank 20 of the bone screw 18 to extend out of the superior bore 51 from the rear side 50 of the body 44, while capturing the head 23 in the countersink/pocket 52 and not allowing it to extend out of the superior bore 51 from the rear side 50 of the body 44. The inferior bore 52 is sized and configured to allow the cylindrical body 27 of a first diameter to extend out of the inferior bore 53 from the rear side 50 of the body 44, while capturing the head 28 of a second diameter that is larger than the first diameter in the countersink/pocket 54 and not allowing it to extend out of the inferior bore 53 from the rear side 40 of the body 44.

A first notch, concavity, cutout or the like (collectively, "first notch") 55 is formed in the first lateral side 47 of the body 44 of the plate 14. The first notch 55 is generally, but not necessarily rounded, and defines a lower projection 56 that helps the first notch 55 form a first seat. The body 44 of the plate 14 has a greater length at the inferior end 46 than at the superior end 45. A second notch 57, concavity, cutout or the like (collectively, "second notch") 57 is formed in the second lateral side 48 of the body 44 of the plate 14. The second notch 57 is generally, but not necessarily rounded, and defines a lower projection 59 and an upper projection 58 that helps the second notch 57 form a second seat.

As seen in FIG. 2 (and other FIGS.), when the plate 14 is connected to the wedge 12, the first notch 55 on the first lateral side 35 of the plate 14 aligns with the first groove 40 on the first lateral side 35 of the wedge 12, and the second notch 57 on the second lateral side 36 of the plate 14 aligns with the second groove 41 on the second lateral side 36 of the wedge 12. The first notch 55/first groove 40 pair is adapted to receive a prong or tang of the surgical instrument 60 (i.e. prong 67, see, e.g., FIG. 9). The second notch 57/second groove 41 pair is adapted to receive another prong or tang of the surgical instrument 60 (i.e. prong 68, see, e.g., FIG. 8).

Figure 8:
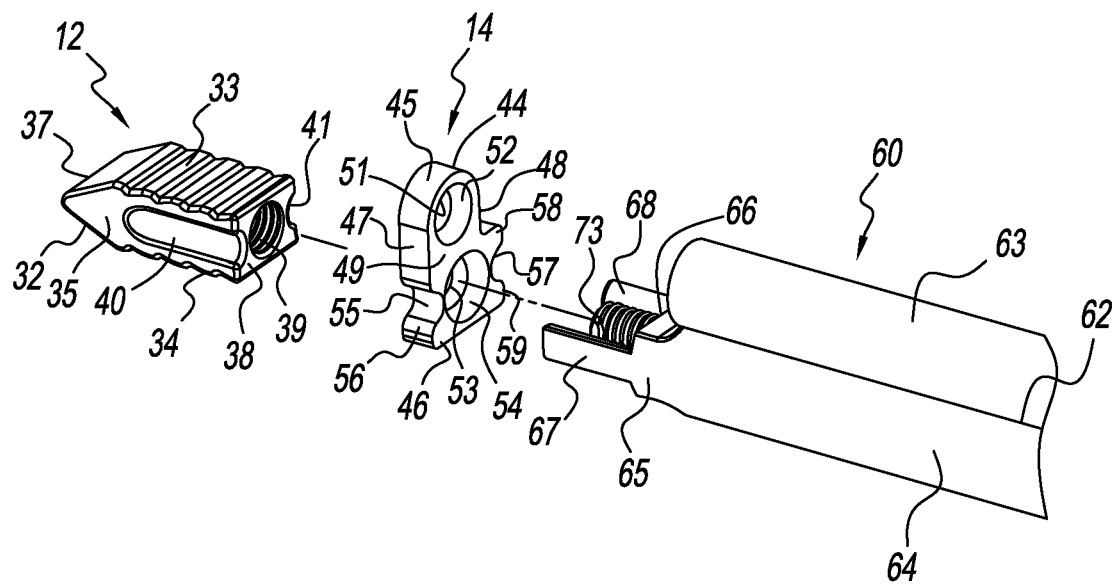
FIG. 8 is an exploded view of the wedge and plate construct of the implant of FIG. 1 relative to a surgical instrument for installing the present implant.

Referring to FIG. 8, there is shown a distal end 66 of a body 62 of the surgical instrument 60 for installing the implant 10. The wedge 12 and the plate 14 are shown ready to be received by the surgical instrument 60. The distal end 66 of the surgical instrument 60 carries the first and second prongs or tangs 67, 68 each extending axially from opposite lateral side of a neck portion 65 of the body 62. The plate 14 is received over a threaded end 73 of the surgical instrument 60, while the wedge 12 is ready to be received on the threaded end 73 and, particularly, the internally threaded bore 39 of the wedge 12 is ready to threadedly engage the threaded end 73 of the surgical instrument 60. As seen in the sectional view of FIG. 10, the body 62 has a superior tube 63 and an inferior tube 64. The superior tube 63 defines a superior cavity 69, while the inferior tube 64 defines an inferior cavity 70. The superior cavity 69 is empty at this point. A rod (surgical instrument component) 72 with the threaded end 73 is axially movably disposed in the superior cavity 69.

Figure 9:
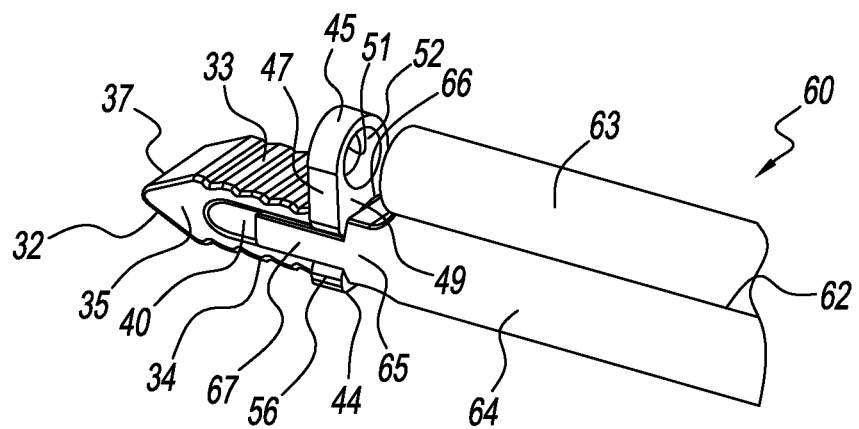
FIG. 9 is a view of the wedge and plate construct received on the surgical instrument of FIG. 8.
Figure 10:
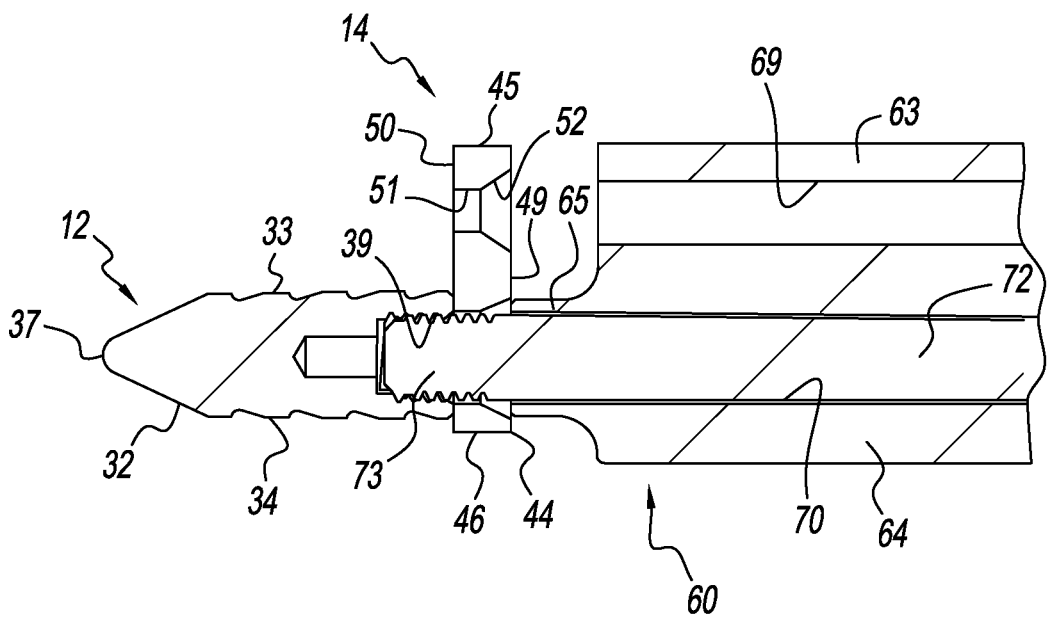
FIG. 10 is an enlarged sectional view of the front end of the present surgical instrument with the wedge and the plate construct received thereon.

FIG. 9 shows the wedge 12 and plate 14 received on the surgical instrument 60, and ready for implantation. FIG. 10 provides a sectional view showing the implant 10 received on the surgical instrument 60.

Figure 11:
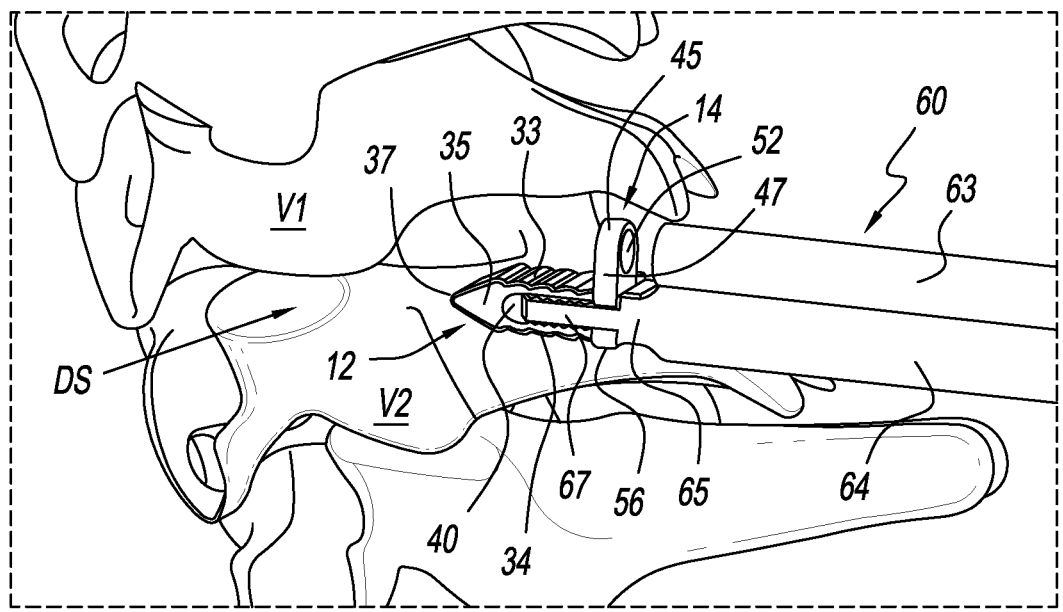
FIG. 11 is a view of a segment of a spine showing the present surgical instrument with the wedge and plate construct held thereon and illustrating introduction of the wedge and plate construct into a spinal facet joint—posteriorly, of a superior vertebra V1 and an inferior vertebra V2, by the surgical instrument during implantation/installation.
Figure 12:
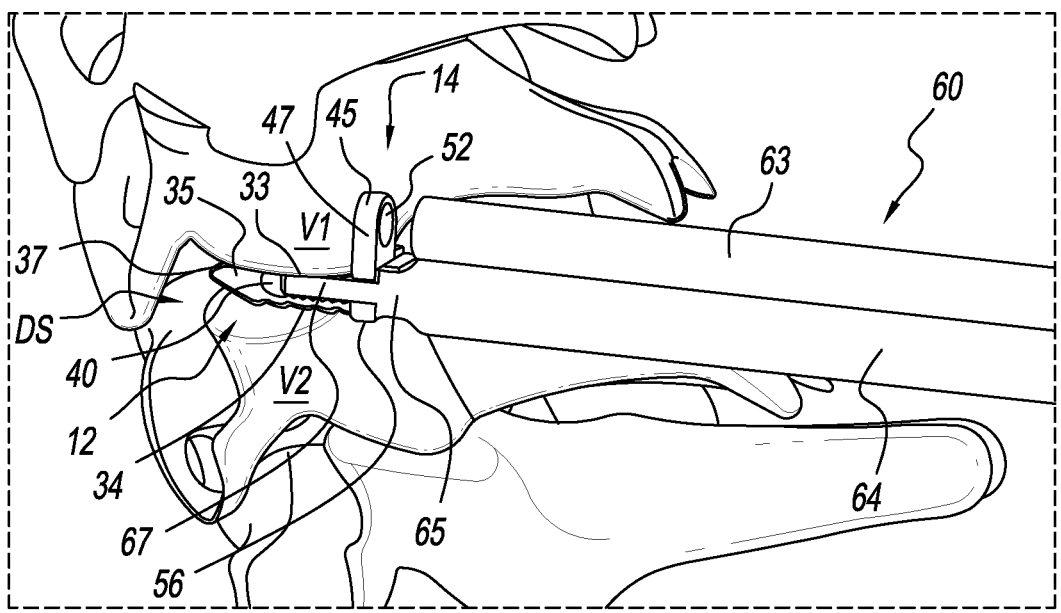
FIG. 12 is a view of the segment of the spine of FIG. 11 showing the present surgical instrument having placed the wedge and plate construct into the spinal facet joint.

FIGS. 11-18 illustrate a method of installing the present implant 10 utilizing the present surgical instrument/tool 60, and/or a method for stabilizing a spinal facet joint utilizing the present implant 10 and the present surgical instrument/tool 60. In FIG. 11, the wedge 12 and plate 14 construct that is held by the surgical instrument 60 is being posteriorly introduced to the facet joint DS. In FIG. 12, the wedge 12 and plate 14 construct has be placed in the spinal facet joint.

Figure 13:
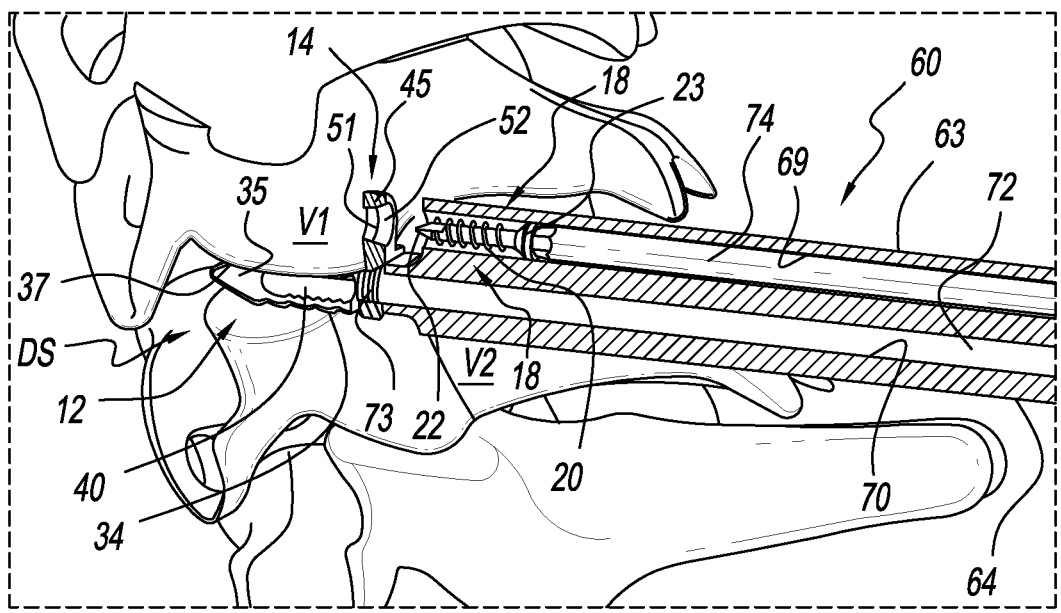
FIG. 13 is a view of the segment of the spine of FIG. 11 showing the present surgical instrument in sectional with the bone screw of the implant of FIG. 1 within a superior tube of the surgical instrument and being advanced through the superior bore of the plate of the implant of FIG. 1 by a screw driving surgical component of the surgical instrument (e.g. a configured rod), and the wedge and plate construct connected to an implant holding surgical component of the surgical instrument (e.g. a configured rod) disposed within an inferior tube of the surgical instrument, the surgical instrument also having prongs that hold the wedge and plate construct during installation.
Figure 14:
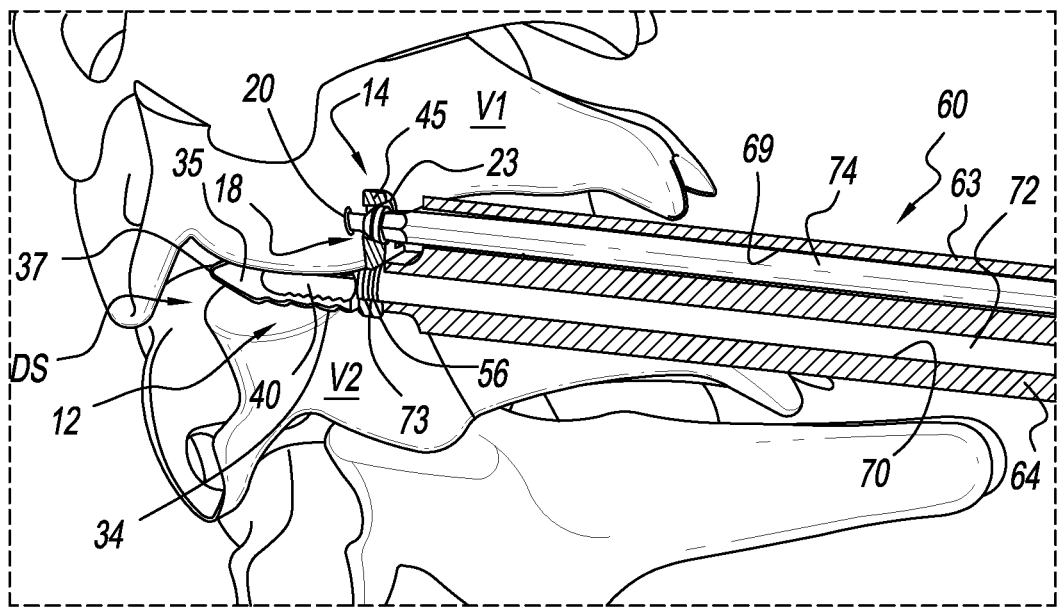
FIG. 14 is the view of FIG. 13 with the bone screw received by the plate and affixed into the superior articular process of superior vertebra V1 of the affected facet joint.
Figure 15:
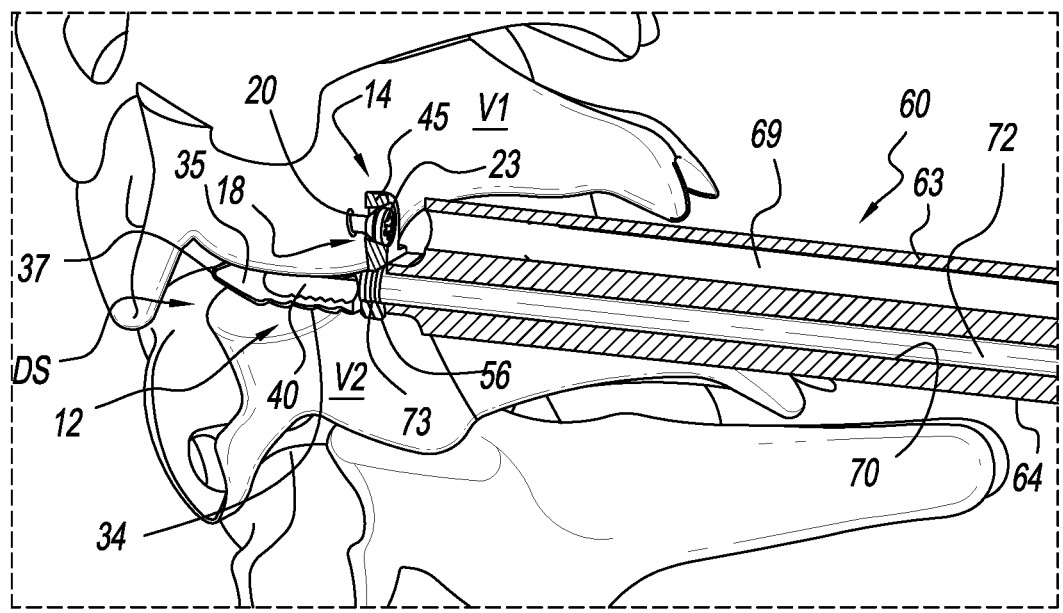
FIG. 15 is the view of FIG. 14 with the screw driving surgical instrument removed from the superior tube of the surgical instrument.
Figure 16:
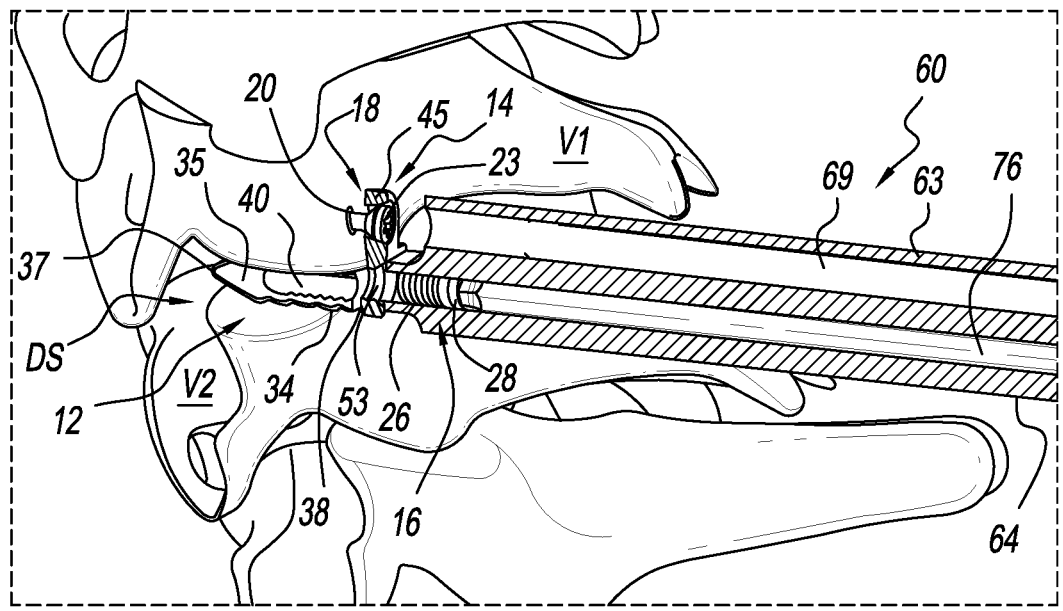
FIG. 16 is the view of FIG. 15 with the installation rod in the inferior tube of the surgical instrument advancing the set screw of the implant of FIG. 1 towards the wedge for attaching the plate to the wedge.
Figure 17:
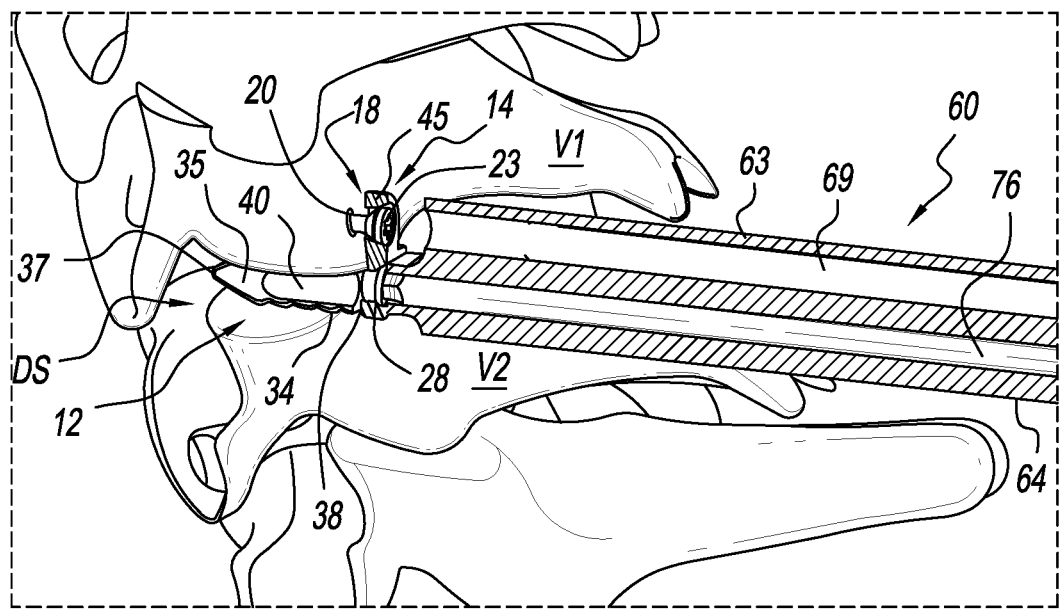
FIG. 17 is the view of FIG. 16 with the set screw received by the plate and wedge.
Figure 18:
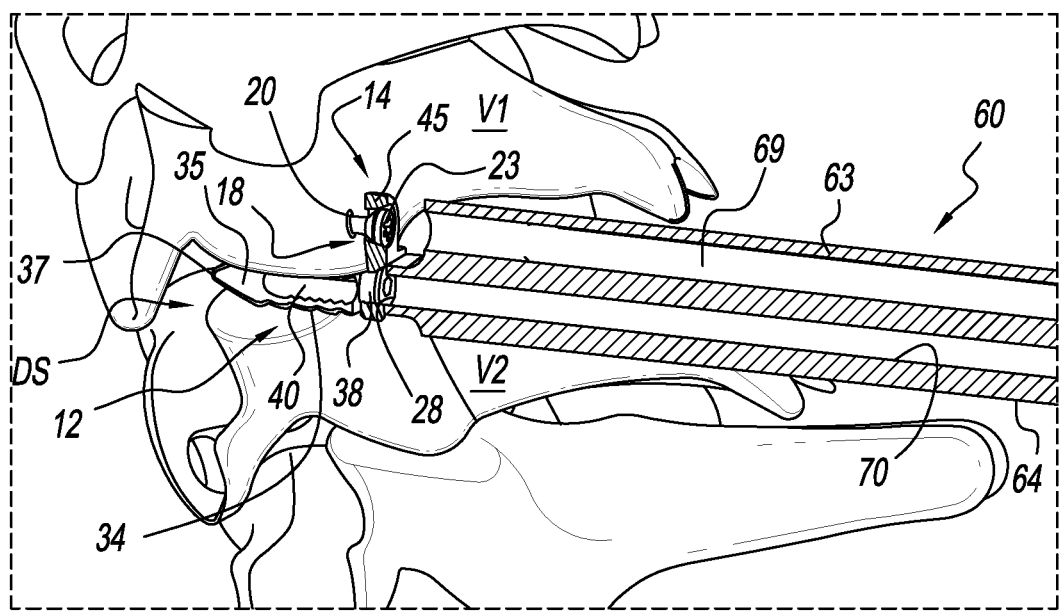
FIG. 18 is the view of FIG. 17 with the installation rod removed from the inferior tube of the surgical instrument/installation tool.

In FIG. 13, the bone screw 18 is being introduced through the superior tube 63 to the superior bore 51 of the plate 14 via a screw driver rod 74. In FIG. 14, the screw driver rod 74 has driven the bone screw 18 into the superior articular process of the facet joint. In FIG. 15, the screw driver rod 74 has been removed from the superior tube 63. In FIG. 16, with the plate secured to the vertebra, the surgical inferior rod component 72 with the temporary set screw/threaded end 73, has been removed, and a surgical instrument component rod 76 carrying the set screw 16 is then introduced into the inferior tube 64. In FIG. 17, the set screw 16 has been installed. In FIG. 18, the surgical instrument component rod 76 of the inferior tube 64 has been removed. The surgical instrument 60 may now disengage from the implant 10.

Figure 19:
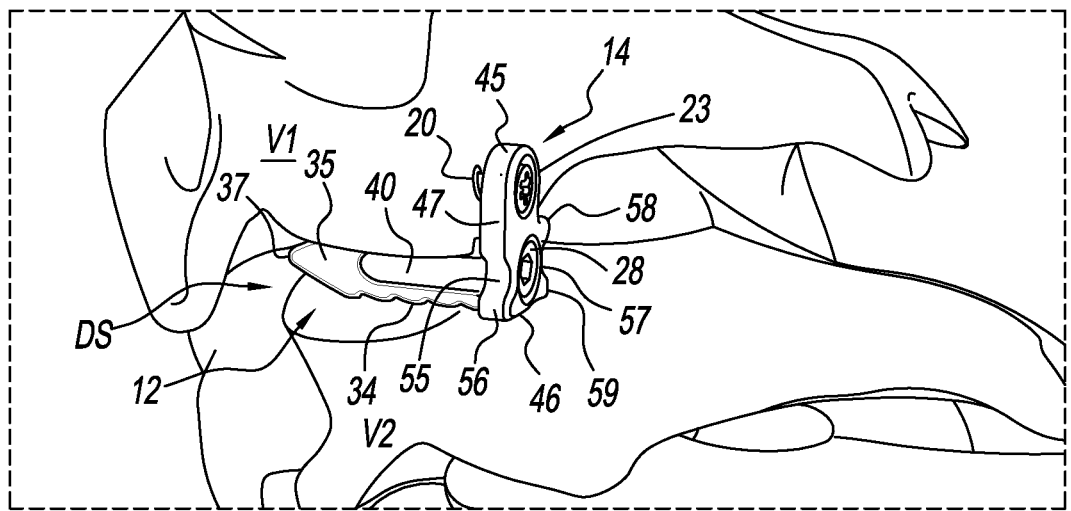
FIG. 19 is a view of the segment of the spine of FIG. 11 with the present implant installed at the facet joint.
Figure 20:
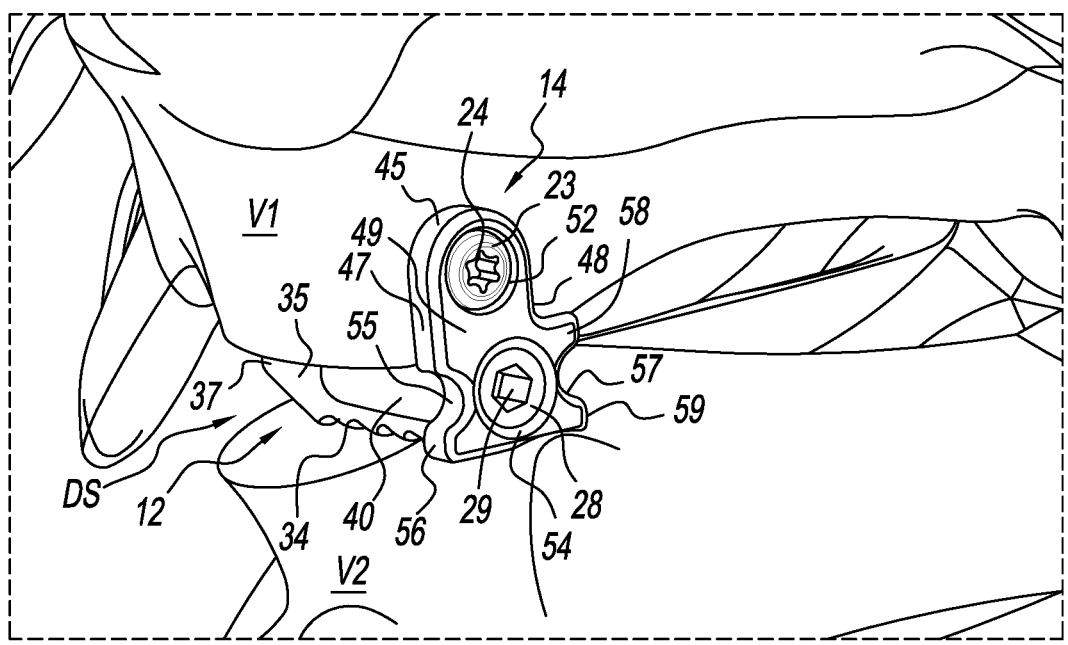
FIG. 20 is a close up view of FIG. 19 showing the installed implant.

FIG. 19 shows one view of the implant 10 installed in a spinal facet joint. FIG. 20 shows an enlarged view of the implant 10 installed in the spinal facet joint.

It should be appreciated that dimensions of the components, structures, and/or features of the present strut may be altered as desired within the scope of the present disclosure.

What is claimed is:

1. An implant for stabilizing a facet joint of the spine comprising:
   a wedge having a length, a posterior end, an anterior end, a superior side extending from the posterior end to the anterior end, an inferior side extending from the posterior end to the anterior end and opposite to the superior side, a first lateral side transverse to and extending between the superior side and the inferior side, a second lateral side transverse to and extending between the superior side and the inferior side and opposite the first lateral side, a first rounded groove in the first lateral side extending a first distance from the anterior end towards the posterior end to at least midway of the length of the wedge, a second rounded groove in the second lateral side and extending a second distance from the anterior end towards the posterior end to at least midway of the length of the wedge, and a threaded bore in the anterior end extending towards the posterior end and adapted to receive one or more threaded components for installing the implant in a spinal facet joint, the posterior end formed as a prism with an elongated ovular apex and defined by a first triangular portion having a first triangular portion base extending from the first lateral side with a first triangular portion apex thereof distal to the first lateral side, a second triangular portion having a second triangular portion base extending from the second lateral side with a second triangular portion apex thereof distal to the second lateral side, a first transverse surface extending angularly from the superior side and having a first transverse surface end, a first transverse surface first lateral side meeting the first triangular portion, a first transverse surface second lateral side meeting the second triangular portion, and a second transverse surface extending angularly from the inferior side and having a second transverse surface end, a second transverse surface first lateral side meeting the first triangular portion, and a second transverse surface second lateral side meeting the second triangular portion, the first triangular portion apex, the second triangular portion apex, the first transverse surface end, and the second transverse surface end all meeting to form the elongated ovular apex of the prism; and
   a plate having a front side, a rear side, a rounded superior end, a planar inferior end configured to rest on an inferior articular process of the spinal facet joint where the wedge is installed, a third lateral side, a fourth lateral side, a single bone screw bore situated in the rounded superior end with the single bone screw bore extending from the front side to the rear side and adapted to receive and capture a bone screw, an unthreaded inferior bore at the planar inferior end extending from the front side to the rear side and adapted to allow the one or more threaded components to pass through from the front side to the rear side, a first rounded notch in the third lateral side extending from the front side to the rear side, and a second rounded notch in the fourth lateral side extending from the front side to the rear side;
   the first rounded notch in the third lateral side of the plate aligning with the first rounded groove of the first lateral side of the wedge to receive a first prong of an implant installation instrument; and
   the second rounded notch in the fourth lateral side of the plate aligning with the second rounded groove of the second lateral side of the wedge to receive a second prong of the implant installation instrument.

2. The implant of claim 1, wherein the one or more threaded components comprises a set screw, the set screw having an externally threaded cylindrical body of a first diameter and defining a first end and a second end, the second end having a head of a second diameter that is greater than the first diameter of the externally threaded cylindrical body for retention of the set screw by the unthreaded inferior bore of the plate, and a configured socket in the head of the second end of the externally threaded cylindrical body adapted to receive a threaded component of the one or more threaded components of the implant installation instrument.

3. The implant of claim 2, wherein the head of the second end reduces in diameter from the second diameter to the first diameter of the externally threaded cylindrical body of the set screw at a neck disposed between the head and the externally threaded cylindrical body.

4. The implant of claim 1, wherein the superior side of the wedge has a first texture, and the inferior side of the wedge has a second texture.

5. The implant of claim 4, wherein the first and second textures comprise serrations.

6. The implant of claim 1, wherein:
   the single bone screw bore in the rounded superior end of the plate has a superior countersink at the front side of the plate; and
   the inferior bore of the planar inferior end of the plate has an inferior countersink at the front side of the plate.

7. An implant for fusing a facet joint of the spine comprising:
   a set screw having an externally threaded cylindrical body of a first diameter defining a first set screw end of the first diameter and a second set screw end of a second diameter that is greater than the first diameter situated opposite the first set screw end, and a socket in the second set screw end;
   a wedge having a length, a posterior end, an anterior end, a superior side extending from the posterior end to the anterior end, an inferior side extending from the posterior end to the anterior end and opposite the superior side, a first lateral side transverse to and extending between the superior side and the inferior side, a second lateral side transverse to and extending between the superior side and the lateral side and opposite the first lateral side, a first rounded groove in the first lateral side extending a first distance from the anterior end towards the posterior end to at least midway of the length of the wedge, a second rounded groove in the second lateral side extending a second distance from the anterior end towards the posterior end to at least midway of the length of the wedge, and a threaded bore in the anterior end extending towards the posterior end and adapted to receive the externally threaded cylindrical body of the set screw, the posterior end formed as a prism with an elongated ovular apex and defined by a first triangular portion having a first triangular portion base extending from the first lateral side with a first triangular portion apex thereof distal to the first lateral side, a second triangular portion having a second triangular portion base extending from the second lateral side with a second triangular portion apex thereof distal to the second lateral side, a first transverse surface extending angularly from the superior side and having a first transverse surface end, a first transverse surface first lateral side meeting the first triangular portion, a first transverse surface second lateral side meeting the second triangular portion, and a second transverse surface extending angularly from the inferior side and having a second transverse surface end, a second transverse surface first lateral side meeting the first triangular portion, and a second transverse surface second lateral side meeting the second triangular portion, the first triangular portion apex, the second triangular portion apex, the first transverse surface end, and the second transverse surface end all meeting to form the elongated ovular apex of the prism; and a plate having a front side, a rear side, a rounded superior end, a planar inferior end configured to rest on an inferior articular process of a facet joint of a spine, a third lateral side, a fourth lateral side, a single bone screw bore situated in the rounded superior end with the single bone screw bore extending from the front side to the rear side and adapted to receive and capture a bone screw, an unthreaded inferior bore at the planar inferior end extending from the front side to the rear side and adapted to allow the set screw to pass through from the front side to the rear side, a first rounded notch in the third lateral side extending from the front side to the rear side, and a second rounded notch in the fourth lateral side extending from the front side to the rear side;

the first rounded notch in the third lateral side of the plate aligning with the first rounded groove of the first lateral side of the wedge to receive a first prong of an implant installation tool; and the second rounded notch in the fourth lateral side of the plate aligning with the second rounded groove of the second lateral side of the wedge to receive a second prong of the implant installation tool.

8. The implant of claim 7, wherein the second set screw end has a head that reduces in diameter from the second diameter to the first diameter of the externally threaded cylindrical body of the set screw at a neck disposed between the head and the externally threaded cylindrical body.

9. The implant of claim 7, wherein the superior side of the wedge has a first texture, and the inferior side of the wedge has a second texture.

10. The implant of claim 9, wherein the first and second textures comprise serrations.

11. The implant of claim 10, wherein:
the single bone screw bore in the rounded superior end of the plate has a superior countersink at the front side of the plate; and the inferior bore of the planar inferior end of the plate has an inferior countersink at the front side of the plate.

12. A surgical kit for use in spinal facet joint fusion surgery, the kit comprising:

a set screw, the set screw having an externally threaded cylindrical body of a first diameter and defining a first end and a second end, the second end having a head of a second diameter that is greater than the first diameter of the externally threaded cylindrical body for retention of the set screw by the inferior bore of the plate, and a configured socket in the head of the second end of the externally threaded cylindrical body;

a bone screw, the bone screw having a shank with external threads, a tip at one end of the shank, and a head at a second end of the shank opposite the tip;

a wedge, the wedge having a length, a posterior end, an anterior end, a superior side extending from the posterior end to the anterior end, an inferior side extending from the posterior end to the anterior end and opposite to the superior side, a first lateral side transverse to extending between the superior side and the inferior side, a second lateral side transverse to extending between the superior side and the inferior side and opposite the first lateral side, a first rounded groove in the first lateral side extending a first distance from the anterior end towards the posterior end to at least midway of the length of the wedge, a second rounded groove in the second lateral side extending a second distance from the anterior end towards the posterior end to at least midway of the length of the wedge, and a threaded bore in the anterior end extending towards the posterior end and adapted to receive the externally threaded cylindrical body of the set screw, the posterior end formed as a prism with an elongated ovular apex and defined by a first triangular portion having a first triangular portion base extending from the first lateral side with a first triangular portion apex thereof distal to the first lateral side, a second triangular portion having a second triangular portion base extending from the second lateral side with a second triangular portion apex thereof distal to the second lateral side, a first transverse surface extending angularly from the superior side and having a first transverse surface end, a first transverse surface first lateral side meeting the first triangular portion, a first transverse surface second lateral side meeting the second triangular portion, and a second transverse surface extending angularly from the inferior side and having a second transverse surface end, a second transverse surface first lateral side meeting the first triangular portion, and a second transverse surface second lateral side meeting the second triangular portion, the first triangular portion apex, the second triangular portion apex, the first transverse surface end, and the second transverse surface end all meeting to form the elongated ovular apex of the prism;

a plate, the plate having a front side, a rear side, a rounded superior end, a planar inferior end configured to rest on an inferior articular process of a facet joint of a spine, a third lateral side, a fourth lateral side, a single bone screw bore situated in the rounded superior end with the single bone screw bore extending from the front side to the rear side and adapted to receive and capture the bone screw, an unthreaded inferior bore at the planar inferior end extending from the front side to the rear side and adapted to allow the set screw to pass through from the front side to the rear side, a first rounded notch in the third lateral side extending from the front side to the rear side, and a second rounded notch in the fourth lateral side extending from the front side to the rear side; and a surgical instrument for installing the wedge, the plate, the bone screw, and the set screw into the facet joint.

13. The surgical kit of claim 12, wherein the surgical instrument comprises an elongate body defining a proximal end and a distal end, an inferior tube having an inferior bore extending from the proximal end of the elongate body to the distal end of the elongate body, a superior tube having a bore extending from the proximal end of the elongate body to the distal end of the elongate body, and first and second prongs extending from the distal end of the inferior tube, the first prong adapted to be received in the first rounded notch in the third lateral side of the plate and the first rounded groove of the first lateral side of the wedge to hold the wedge, the second prong adapted to be received in the second rounded notch in the fourth lateral side of the plate and the second rounded groove of the second lateral side of the wedge to hold the wedge.

14. The surgical kit of claim 13, wherein the surgical instrument further comprises:
a superior rod configured for movable reception in the superior tube, the superior rod having a distal end adapted for engaging and installing the bone screw; and
an inferior rod configured for movable reception in the inferior tube, the inferior rod having a distal end adapted to engage the wedge via the threaded bore of the wedge and for engaging and installing the set screw.

15. A method for spinal facet joint stabilization, comprising:
providing a spine implant having:
a set screw, the set screw having an externally threaded cylindrical body of a first diameter and defining a first end and a second end, the second end having a head of a second diameter that is greater than the first diameter of the externally threaded cylindrical body for retention of the set screw by the inferior bore of the plate, and a configured socket in the head of the second end of the externally threaded cylindrical body;
a bone screw, the bone screw having a shank with external threads, a tip at one end of the shank, and a head at a second end of the shank opposite the tip;
a wedge, the wedge having a length, a posterior end, an anterior end, a superior side extending from the posterior end to the anterior end, an inferior side extending from the posterior end to the anterior end and opposite the superior side, a first lateral side transverse to extending between the superior side and the inferior side, a second lateral side transverse to extending between the superior side and the inferior side and opposite the first lateral side, a first rounded groove in the first lateral side extending a first distance from the anterior end towards the posterior end to at least midway of the length of the wedge, a second rounded groove in the second lateral side extending a second distance from the anterior end towards the posterior end to at least midway of the length of the wedge, and a threaded bore in the anterior end extending towards the posterior end and adapted to receive the externally threaded cylindrical body of the set screw, the posterior end formed as a prism with an elongated ovular apex and defined by a first triangular portion having a first triangular portion base extending from the first lateral side with a first triangular portion apex thereof distal to the first lateral side, a second triangular portion having a second triangular portion base extending from the second lateral side with a second triangular portion apex thereof distal to the second lateral side, a first transverse surface extending angularly from the superior side and having a first transverse surface end, a first transverse surface first lateral side meeting the first triangular portion, a first transverse surface second lateral side meeting the second triangular portion, and a second transverse surface extending angularly from the inferior side and having a second transverse surface end, a second transverse surface first lateral side meeting the first triangular portion, and a second transverse surface second lateral side meeting the second triangular portion, the first triangular portion apex, the second triangular portion apex, the first transverse surface end, and the second transverse surface end all meeting to form the elongated ovular apex of the prism; and
a plate, the plate having a front side, a rear side, a rounded superior end, a planar inferior end configured to rest on an inferior articular process of a facet joint of a spine, a third lateral side, a fourth lateral side, a single bone screw bore situated in the rounded superior end with the single bone screw bore extending from the front side to the rear side and adapted to receive and capture the bone screw, an unthreaded inferior bore at the planar inferior end extending from the front side to the rear side and adapted to allow the set screw to pass through from the front side to the rear side, a first rounded notch in the third lateral side extending from the front side to the rear side, and a second rounded notch in the fourth lateral side extending from the front side to the rear side;
providing a surgical instrument that is configured to facilitate installation of the spine implant, the surgical instrument having:
an elongate body defining a proximal end and a distal end, an inferior tube having an inferior bore extending from the proximal end of the elongate body to the distal end of the elongate body, a superior tube having a superior bore extending from the proximal end of the elongate body to the distal end of the elongate body, and first and second prongs extending from the distal end of the inferior tube, the first prong adapted to be received in the first rounded notch in the third lateral side of the plate and the first rounded groove of the first lateral side of the wedge to hold the wedge, the second prong adapted to be received in the second rounded notch in the fourth lateral side of the plate and the second rounded groove of the second lateral side of the wedge to hold the wedge; and surgically installing the spine implant into the facet joint of the spine using the surgical instrument.

16. The method of claim 15 wherein surgical instrument further comprises:
a superior rod configured for movable reception in the superior tube, the superior rod having a distal end adapted for engaging and installing the bone screw; and
an inferior rod configured for movable reception in the inferior tube, the inferior rod having a distal end adapted to engage the wedge via the threaded bore of the wedge and for engaging and installing the set screw.

* * * * *